(12) United States Patent
Purpura et al.

(10) Patent No.: US 7,678,768 B2
(45) Date of Patent: Mar. 16, 2010

(54) PHYSIOLOGICALLY-ACTIVE COMPOSITION BASED ON COLLAGEN

(75) Inventors: Martin Purpura, Bonn (DE); Ralf Jäger, Freising (DE); Karim Balan, Regensburg (DE); Dietrich Paper, Maxhütte-Haidhof (DE)

(73) Assignee: Cargill Incorporated, Wayzata, MN (US)

( * ) Notice: Subject to any disclaimer, the term of this patent is extended or adjusted under 35 U.S.C. 154(b) by 483 days.

(21) Appl. No.: 11/658,437

(22) PCT Filed: Jul. 27, 2005

(86) PCT No.: PCT/EP2005/008151

§ 371 (c)(1),
(2), (4) Date: Jan. 26, 2007

(87) PCT Pub. No.: WO2006/010606

PCT Pub. Date: Feb. 2, 2006

(65) Prior Publication Data

US 2009/0005322 A1    Jan. 1, 2009

(30) Foreign Application Priority Data

Jul. 28, 2004    (DE)    ........................ 10 2004 036 577

(51) Int. Cl.
*A61K 38/00*    (2006.01)
*A61K 33/00*    (2006.01)
(52) U.S. Cl. ........................................ 514/12; 424/774
(58) Field of Classification Search .................. 424/774; 514/12

See application file for complete search history.

(56) References Cited

U.S. PATENT DOCUMENTS

| 6,224,871 | B1 | 5/2001 | Hastings et al. |
| 6,514,540 | B1 | 2/2003 | Sobczak |
| 2001/0024664 | A1 | 9/2001 | Obukowicz et al. |
| 2001/0048952 | A1 | 12/2001 | Siskind |
| 2002/0086070 | A1 | 7/2002 | Kuhrts |
| 2003/0069171 | A1 | 4/2003 | Petito et al. |
| 2004/0086581 | A1 | 5/2004 | Jones |

FOREIGN PATENT DOCUMENTS

| DE | 100 47 835 A1 | 4/2002 |
| EP | 0 577 143 A2 | 1/1994 |

*Primary Examiner*—Maryam Monshipouri
(74) *Attorney, Agent, or Firm*—Ping Wang; Morris, Manning & Martin, LLP

(57) ABSTRACT

The present invention concerns a physiologically active composition which contains an enzymatically hydrolysed collagen as the active component I and at least one component of the non-vitamin type having anti-oxidative and/or anti-inflammatory properties as the active component II. Collagen of animal origin that is soluble in cold water comes into particular consideration as component I and a fermentation broth or a plant extract comes into particular consideration as component II. This composition which is designed in particular as a food supplement or functional food can be used to prevent inflammatory and/or degenerative symptoms in particular with a chronic course such as for example arthritis and arthroses or to successfully treat these symptoms. The claimed composition can be used above all by professional, leisure and recreational athletes who suffer in particular from strained joint functions.

16 Claims, No Drawings

PHYSIOLOGICALLY-ACTIVE COMPOSITION BASED ON COLLAGEN

This is a §371 of PCT/EP2005/008151 filed Jul. 27, 2005, which claims priority from German Patent Application No. 10 2004 036 577.6 filed Jul. 28, 2004.

The present invention concerns a physiologically active composition based on collagen.

Collagen is a natural fibre protein which is the main component of supporting and connective tissue and is found especially in the skin, tendons and bones. Thus collagen is one of the most important proteins of connective tissue and constitutes about 30% of the total protein mass of humans. Collagens are among the few proteins whose sequence has a periodic structure over long sections and forms a very rigid helix comprising three chains. In general one differentiates between several types of collagen which differ in their structure and sequence where the collagen pattern is typical for the respective tissue. Collagen type I is for example mainly found in bones, tendons, in the skin as well as in large blood vessels and the cornea; collagen type II is mainly involved in costal cartilage and horny skin; finally collagen types III and IV form the major blood vessels and the skin and they are involved in the formation of the basal membrane.

Collagen as an endogenous substance has been used for a long time in connection with the treatment of degenerative joint diseases and in particular predominantly for the treatment of arthroses and arthritic forms.

Inflammatory processes and associated pain forms are the result of a complex interplay of various pathological processes in degenerative joint diseases. The genesis and progression of such inflammatory and pain states is almost always based on the actual inflammatory reaction. However, this is also associated with changes in the vascular system and the swellings, rubescence and fever symptoms that result from these changes, and also changes in the sensitivity of the pain receptors and changes in the transmission and processing of pain by nerves in the central nervous system as well as modulation of the immune system or by the immune system play an important role in degenerative joint diseases.

None of the said fields can be considered to be isolated since for example the release of certain inflammatory mediators lead to a dilation of the vessels and thus to an increased immigration of cells of the immune system as well as to a reduction in the pain threshold. The immigrated immune cells in turn subsequently amplify the inflammatory process through the degradation of tissue structures and the release of further inflammatory mediators, where the concurrently released amounts of histamine result in an additional increase in blood flow and to pain due to a further decrease in the pain threshold.

Central mediators of the inflammatory process play a central role in the process of degenerative joint diseases and associated secondary disease forms where prostaglandins and leukotrienes take key positions since prostaglandins induce the release of lytic enzymes and amplify the inflammatory process by increasing the number of cytokine receptors and thus the reactivity of the involved cells. This is also concomitantly associated with a decrease in the pain threshold. Cyclooxygenases (COX-1 and COX-2) which catalyse key reactions in the formation of prostaglandins from arachidonic acid are also involved.

Like the prostaglandins, leukotrienes are also formed from arachidonic acid in which 5-lipoxygenase plays an important role. Other enzymes that play a role in the changes in the vascular system or in the pain process are NO-synthase, histamine oxidase and monooxygenases and oxidoreductases in general.

Numerous literature references are known from the prior art which give information on methods of treating degenerative joint diseases with the aid of collagen.

Thus EP 0 254 289 B1 describes agents for the treatment of arthroses which contain a flavourless or flavour-neutral, enzymatically hydrolysed collagen having an average molecular weight of 10 to 80 kilodaltons. The hydrolysed collagen that is used is derived from animal skin, animal bones or other adequately purified connective tissue. Accordingly the collagen is hydrolysed mainly by enzymatic means, the conditions being selected such that a certain molecular weight range is obtained. Depending on the manufacturing conditions the collagen hydrolysates have a larger or smaller number of carboxyl groups and amino groups and they have different isoelectric pH ranges. The hydrolysed collagens used under this property right are for example marketed under the product names "Gelita-Sol" (DGF Stoess AG) and "Arthred" (Degussa Food Ingredients GmbH).

The following positive findings were ascertained in the study published in EP 0 254 289 on patients with degenerative diseases of the hip joint and/or knee joint: improvements in the initial pain and initial stiffness, decrease of exercise and fatigue pain as well as a reduced pain upon pressure over the articular space and a reduction in end phase pain. With regard to the movability of the hip joints, a considerably improved flexion was found which was ascertained to a more pronounced extent for the movability of the knee joints.

A method for increasing the cartilaginous mass in joints is known from U.S. Pat. No. 6,211,143. In this method hydrolysed gelatin having a molecular weight between 2 and 100 kilodaltons is administered orally. In addition at least one representative of the vitamin B group and/or an organic or inorganic magnesium compound can be added to the daily doses of gelatin.

The method according to this US protective right can be regarded as an improvement of the generally known administration of enzymatically hydrolysed gelatin of which only assumptions about the precise mechanism of action were known at that time. Hence it was assumed that hydrolysed collagen could improve the symptoms of arthritic damage. A certain tolerance towards proteins taken orally was also assumed. In this connection it was in particular contested that larger cartilaginous masses could be formed by taking precursors of collagen synthesis such as hydrolysed gelatin.

As a rule "gelatin" is collagen treated usually with warm alkali which can be dissolved by this measure. Gelatin solutions form stiff jellies on cooling. Thus gelatins are proteins that are obtained from collagen. In order to prevent potential allergic reactions when administering gelatins, gelatins which have been obtained from collagen by extraction are additionally subjected to a controlled enzymatic or chemical hydrolysis in order to thus obtain defined short-chain peptides which are in turn completely metabolized.

Another product which is used for the prevention or treatment of degenerative joint diseases is "Arthred" (Degussa Food Ingredients GmbH). This product is also an enzymatically hydrolysed collagen consisting of short-chain peptides having a low total molecular weight of about 3 kilodaltons. The collagen-based peptides in Arthred are excellently soluble in cold water due to the selected molecular weights.

As already described degenerative joint diseases are not least also inflammatory processes. The prior art offers numerous natural preparations to treat inflammations especially in the region of the joints. In this connection compounds having anti-oxidative properties such as for example flavonoids are particularly suitable. Above all plant extracts some of which can contain a large number of different classes of compounds and compounds having antioxidative properties are also offered in a variety of application forms.

In this connection the already mentioned cyclooxygenases are also of interest and thus the corresponding COX-1 and COX-2 inhibitors play an important role in inflammatory processes. Rutaecarpin, kaempferol and humolone are particularly worthy of mention.

The following table 1 names plants or parts thereof having a pronounced COX-2 inhibitory activity and the main ingredients that are responsible for this activity:

TABLE 1

1.1 APIGENIN

*Achillea millefolium* L. - Milfoil, Yarrow; found in Plant
*Anisochilus carnosus* WALL. - Panjiri-ka Pat; found in Plant
*Apium graveolens* L. - Celery; found in Plant
*Araucaria bidwillii* HOOK. - Monkey puzzle; found in Leaf
*Artemisia dracunculus* L. - Tarragon; found in Plant
*Camellia sinensis* (L.) KUNTZE - Tea; found in Leaf
*Centaurea calcitrapa* L. - Star-Thistle; found in Plant
*Chamaemelum nobile* (L.) ALL. - Garden Camomile, Perennial Camomile, Roman Camomile; found in Plant
*Colchicum autumnale* L. - Autumn Crocus, Meadow Saffron; found in Tuber
*Conyza canadensis* (L.) CRONQ. - Butterweed, Hogweed, Horseweed; found in Plant
*Coriandrum sativum* L. - Chinese Parsley, Cilantro, Coriander; found in Fruit
*Daphne genkwa* SIEB & ZUCC. - Yuan Hua; found in Flower
*Daucus carota* L. - Carrot; found in Fruit
*Digitalis purpurea* L. - Purple Foxglove; found in Flower
*Echinacea* spp - Coneflower, *Echinacea*; found in Leaf
*Ginkgo biloba* L. - *Ginkgo*, Maidenhair Tree; found in Leaf
*Glechoma hederacea* L. - Alehoof; found in Plant
*Glycyrrhiza glabra* L. - Commom Licorice, Licorice, Licorice-Root, Smooth Licorice; found in Root
*Hydnocarpus wightiana* BLUME - Hindi Chaulmoogra; found in Seed
*Jatropha gossypifolia* L. - Spanish Physic Nut; found in Leaf
*Linum usitatissimum* L. - Flax, Linseed; found in Plant
*Lycopodium clavatum* L. - Antler Herb, Clubmoss; found in Plant
*Marrubium vulgare* L. - Horehound, White Horehound; found in Plant
*Matricaria recutita* L. - Annual Camomile, German Camomile, Wild Camomile; found in Plant
*Mentha aquatica* L. - Water Mint; found in Plant
*Mentha spicata* L. - Hortela da Folha Miuda, Spearmint; found in Leaf
*Mentha x rotundifolia* (L.) HUDSON - Applemint; found in Shoot
*Ocimum basilicum* L. - Basil, Cuban Basil, Sweet Basil; found in Plant
*Olea europaea* subsp. *europaea* - Olive; found in Leaf
*Origanum vulgare* L. - Common Turkish Oregano, European Oregano, Oregano, Pot Marjoram, Wild Marjoram, Wild Oregano; found in Plant
*Passiflora incarnata* L. - Manzana de Mayo, Mayapple, Passionflower; found in Plant
*Perilla frutescens* (L.) BRITTON - *Perilla*; found in Seed
*Petroselinum crispum* (MILLER) NYMAN EX A. W. HILLL - Parsley; found in Plant
*Phaseolus vulgaris* subsp. var. *vulgaris* - Black Bean, Dwarf Bean, Field Bean, Flageolet Bean, French Bean, Garden Bean, Green Bean, Haricot, Haricot Bean, Haricot Vert, Kidney Bean, Navy Bean, Pop Bean, Popping Bean, Snap Bean, String Bean, Wax Bean; found in Plant
*Phoenix dactylifera* L. - Date Palm; found in Stem
*Plantago major* L. - Common Plantain; found in Leaf
*Pogostemon cablin* (BLANCO) BENTH. - Patchouli; found in Plant
*Prosopis juliflora* (SW.) DC. - Mesquite; found in Plant
*Prunus cerasus* L. - Sour Cherry; found in Plant
*Rosmarinus officinalis* L. - Rosemary; found in Plant
*Salix alba* L. - White Willow; found in Bark
*Salvia officinalis* L. - Sage; found in Plant
*Scutellaria galericulata* L. - Marsh Skullcap; found in Plant
*Silybum marianum* (L.) GAERTN. - Lady's Thistle, Milk Thistle; found in Fruit
*Tanacetum vulgare* L. - Tansy; found in Plant
*Teucrium polium* L. - Golden Germander; found in Plant
*Thymus serpyllum* L. - Creeping Thyme; found in Plant
*Thymus vulgaris* L. - Common Thyme, Garden Thyme, Thyme; found in Plant
*Triticum aestivum* L. - Wheat; found in Seed 1.2 BAICALEIN

*Plantago major* L. - Common Plantain; found in Leaf
*Scutellaria baicalensis* GEORGI - Baikal Skullcap, Chinese Skullcap, Huang Qin; found in Root
*Scutellaria galericulata* L. - Marsh Skullcap; found in Plant
*Scutellaria* sp; found in Leaf

TABLE 1-continued

1.3 BERBERIN

*Adonis vernalis* L. - Spring Adonis; found in Plant
*Andira inermis* HBK - Cabbage Bark; found in Bark
*Argemone mexicana* L. - Prickly Poppy; found in Plant
*Berberis vulgaris* L. - Barberry; found in Plant
*Chelidonium majus* L. - Celandine; found in Plant
*Coptis chinensis* FRANCH. - Chinese Goldthread, Huang-Lian, Huang-Lien; found in Rhizome
*Coptis japonica* (THUNB.) MAKINO - Huang-Lia, Huang-Lian, Huang-Lien, Japanese Goldthread; found in Rhizome
*Coptis* spp - Generic Goldthread; found in Rhizome
*Corydalis* spp - Fumewort; found in Plant
*Eschscholzia californica* subsp. *californica* - California Poppy; found in Shoot
*Hydrastis canadensis* L. - Goldenseal; found in Root
*Macleaya cordata* R. BROWN - Plume Poppy; found in Plant
*Mahonia aquifolium* (PURSH) NUTT. - Blue Barberry, Holly Barberry, Holly Mahonia, Mountain Grape, Oregon Grape; found in Root
*Menispermum canadense* L. - Moonseed; found in Plant
*Papaver somniferum* L. - Opium Poppy, Poppyseed Poppy; found in Plant
*Phellodendron amurense* RUPR. - Amur Cork Tree, Huang Bai, Huang Po, Po Mu; found in Bark
*Podophyllum hexandrum* ROYLE - Himalayan Mayapple; found in Rhizome
*Podophyllum peltatum* L. - Mayapple; found in Plant
*Sanguinaria canadensis* L. - Bloodroot; found in Root
*Zanthoxylum alatum* ROXB. - Indian Prickly Ash, Wartara Oil Tree; found in Bark
*Zanthoxylum americanum* MILL. - Northern Prickly Ash; found in Plant

1.4 CINNAMALDEHYDE

*Cinnamomum verum* J. PRESL - Ceylon Cinnamon, Cinnamon Bark 30,000 ppm
*Cinnamomum aromaticum* NEES - Canela de la China (Sp.), Canelero chino (Sp.), Canelle de Cochinchine (Fr.), Cannelier Casse (Fr.), Cannelier de Chine (Fr.), Cassia, Cassia Bark, Cassia Lignea, China Junk Cassia, Chinazimt (Ger.), Chinese Cassia, Chinese Cinnamon, Chinesischer Zimtbaum (Ger.), Kashia-Keihi (Jap.), Saigon Cinnamon, Zimtcassie (Ger.) Bark 1,900 ppm
*Hyacinthus orientalis* L. - Hyacinth Flower 6.9 ppm
*Syzygium aromaticum* (L.) MERR. & L. M. PERRY - Clove, Clovetree Flower 1 ppm
*Cnicus benedictus* L. - Blessed Thistle Plant
*Commiphora myrrha* (NEES) ENGL. - African Myrrh, Herabol Myrrh, Mirra (Sp. It.), Myrrh, Myrrhe (Fr., Ger.), Somali Myrrh Resin, Exudate, Sap AYL
*Lavandula* sp - Lavender Plant JBH
*Lycopersicon esculentum* MILLER - Tomato Fruit
*Melaleuca bracteata* F. VON MUELL. - Bracteate Tea-Tree Leaf GEO
*Myroxylon balsamum* (L.) HARMS - Peru Balsam, Tolu Balsam Plant
*Pimenta dioica* (L.) MERR. - Allspice, Clover-Pepper, Jamaica-Pepper, Pimenta, Pimento Plant
*Pogostemon cablin* (BLANCO) BENTH. - Patchouli Plant
*Rosa damascena* MILLER - Damask Rose Essential Oil
*Tamarindus indica* L. - Indian Tamarind, Kilytree, Tamarind Fruit

1.5 CIRSILINEOL

*Artemisia capillaris* THUNB. - Capillary Wormwood; found in Plant
*Artemisia dracunculus* L. - Tarragon; found in Plant
*Salvia officinalis* L. - Sage; found in Plant
*Salvia tomentosa* - Sage; found in Leaf
*Sideritis* sp; found in Leaf
*Thymus vulgaris* L. - Common Thyme, Garden Thyme, Thyme; found in Leaf

1.6 CURCUMIN

*Curcuma longa* L. - Indian Saffron, Turmeric; found in Rhizome
*Curcuma xanthorrhiza* ROXB. - Javan Turmeric, Temu Lawak; found in Rhizome
*Curcuma zedoaria* (CHRISTM.) ROSCOE - Shoti, Zedoary; found in Rhizome
*Zingiber officinale* ROSCOE - Ginger; found in Plant

1.7 EUGENOL

*Acacia farnesiana* (L.) WILLD. - Cassie, Huisache, Opopanax, Popinac, Sweet Acacia; found in Flower
*Achillea millefolium* L. - Milfoil, Yarrow; found in Plant
*Acorus calamus* L. - Calamus, Flagroot, Myrtle Flag, Sweet Calamus, Sweetflag, Sweetroot; found in Rhizome
*Ageratum conyzoides* L. - Mexican ageratum; found in Shoot
*Alpinia galanga* (L.) SW. - Greater Galangal, Languas, Siamese Ginger; found in Rhizome
*Alpinia officinarum* HANCE - Chinese Ginger, Lesser Galangal; found in Rhizome
*Anethum graveolens* L. - Dill, Garden Dill; found in Plant
*Apium graveolens* L. - Celery; found in Plant
*Artemisia capillaris* THUNB. - Capillary Wormwood; found in Essential Oil
*Artemisia dracunculus* L. - Tarragon; found in Shoot
*Boronia megastigma* NEES ex BARTL. - Scented Boronia; found in Flower TABLE 1-continued

*Calamintha nepeta* subsp. *glandulosa* (REQ.) P. W. BALL - Turkish Calamint; found in Shoot
*Camellia sinensis* (L.) KUNTZE - Tea; found in Fruit
*Cananga odorata* (LAM.) HOOK. f. & THOMSON - Cananga, Ylang-Ylang; found in Flower
*Capsicum annuum* L. - Bell Pepper, Cherry Pepper, Cone Pepper, Green Pepper, Paprika, Sweet Pepper; found in Fruit
*Cinnamomum aromaticum* NEES - Canela de 1a China (Sp.), Canelero chino (Sp.), Canelle de Cochinchine (Fr.), Cannelier Casse (Fr.), Cannelier de Chine (Fr.), Cassia, Cassia Bark, Cassia Lignea, China Junk Cassia, Chinazimt (Ger.), Chinese Cassia, Chinese Cinnamon, Chinesischer Zimtbaum (Ger.), Kashia-Keihi (Jap.), Saigon Cinnamon, Zimtcassie (Ger.); found in Plant
*Cinnamomum camphora* (L.) NEES & EBERM. - Camphor, Ho Leaf; found in Plant
*Cinnamomum verum* J. PRESL - Ceylon Cinnamon, Cinnamon; found in Bark
*Cistus ladaniferus* L. - Ambreine, Gum Cistus, Labdanum, Rockrose; found in Leaf
*Coffea arabica* L. - Coffee; found in Seed
*Commiphora myrrha* (NEES) ENGL. - African Myrrh, Herabol Myrrh, Mirra (Sp. It.), Myrrh, Myrrhe (Fr., Ger.), Somali Myrrh; found in Resin, Exudate, Sap
*Croton eluteria* (L.) SW. - Cascarilla; found in Bark
*Cuminum cyminum* L. - Cumin; found in Fruit
*Curcuma longa* L. - Indian Saffron, Turmeric; found in Essential Oil
*Cymbopogon winterianus* JOWITT - Java Citronella, Mahapengiri; found in Plant
*Cynara cardunculus* subsp. *cardunculus* - Artichoke; found in Essential Oil
*Daucus carota* L. - Carrot; found in Seed
*Drimys winteri* FORSTER & FORSTER f. - Winter's Bark; found in Bark
*Elsholtzia blanda* BENTH. - Bantaluki, Bantulsi; found in Shoot
*Eucalyptus citriodora* HOOK. - Citron-Scented Gum, Lemon Eucalyptus, Lemon-Scented Gum, Spotted Gum; found in Leaf
*Glycyrrhiza glabra* L. - Commom Licorice, Licorice, Licorice-Root, Smooth Licorice; found in Root
*Helianthus annuus* L. - Girasol, Sunflower; found in Flower
*Helichrysum angustifolium* DC. - Everlasting, Immortelle; found in Plant
*Humulus lupulus* L. - Hops; found in Essential Oil
*Hyacinthus orientalis* L. - Hyacinth; found in Flower
*Hyssopus officinalis* L. - Hyssop; found in Flower, Leaf
*Iris x germanica* L. - Orris; found in Rhizome
*Jasminum officinale* L. - Jasmine, Poet's Jessamine; found in Flower
*Juglans regia* L. - English Walnut; found in Leaf
*Lantana camara* L. - Lantana, Wild Sage; found in Leaf
*Laurus nobilis* L. - Bay, Bay Laurel, Bayleaf, Grecian Laurel, Laurel, Sweet Bay; found in Leaf
*Lavandula latifolia* MEDIK. - Aspic, Broad-Leaved Lavender, Spike Lavender; found in Plant
*Lavandula x intermedia* EMERIC ex LOIS - Dutch Lavender, Lavandin; found in Plant
*Levisticum officinale* KOCH - Lovage; found in Root
*Ligustrum japonicum* THUNB. - Japanese Privet, Ligustri Fructus; found in Flower
*Lycopersicon esculentum* MILLER - Tomato; found in Fruit
*Magnolia kobus* DC. - Hsin-I, Xin-Yi; found in Flower
*Melaleuca bracteata* F. VON MUELL. - Bracteate Tea-Tree; found in Leaf
*Melaleuca viridiflora* SOLAND.EX GAERTN. - Broad-Leaf Tea-Tree, Niaouli; found in Leaf
*Melia azedarach* L. - Chinaberry; found in Wood
*Mentha arvensis* var. *piperascens* MALINV. EX L. H. BAILEY - Cornmint, Field Mint, Japanese Mint; found in Essential Oil
*Mentha pulegium* L. - European Pennyroyal; found in Plant
*Mentha spicata* L. - Hortela da Folha Miuda, Spearmint; found in Leaf
*Mentha x piperita* subsp. nothosubsp. *piperita* - Peppermint; found in Essential Oil
*Micromeria congesta* BOISS. & HAUSSKN. - Kaya Yarpuzu; found in Leaf
*Micromeria fruticosa* subsp. *barbata* (BOISS. & KY.) P. H. DAVIS - Tea Hyssop, Zopha, Zuta; found in Shoot
*Micromeria myrtifolia* BOISS. & HOHEN - Dagcayi, Haydarotu, Topukcayi; found in Shoot
*Morus alba* L. - Sang-Pai-Pi, White Mulberry; found in Plant
*Myristica fragrans* HOUTT. - Mace, Muskatnussbaum (Ger.), Nutmeg, nogal moscado (Sp.), nuez moscada (Sp.); found in Seed
*Myroxylon balsamum* (L.) HARMS - Peru Balsam, Tolu Balsam; found in Plant
*Narcissus tazetta* L. - Daffodil; found in Flower
*Nicotiana tabacum* L. - Tobacco; found in Leaf
*Ocimum basilicum* L. - Basil, Cuban Basil, Sweet Basil; found in Leaf, Plant
*Ocimum canum* SIMS - Hoary Basil; found in Shoot
*Ocimum gratissimum* L. - Agbo, Shrubby Basil; found in Plant, Seed, Shoot
*Ocimum kilimandscharicum* GUERKE - African Blue Basil, Kenyan Perennial Basil; found in Flower, Shoot
*Ocimum sanctum* L. - Holy Basil, Tulsi; found in Leaf
*Ocimum* sp - Basil; found in Plant
*Ocimum suave* WILLD. - Kenyan Tree Basil; found in Shoot
*Oenanthe javanica* (BLUME) DC. - Javan Water Dropwort; found in Shoot
*Origanum majorana* L. - Marjoram, Sweet Marjoram; found in Plant

TABLE 1-continued

*Origanum minutiflorum* O. SCHWARZ & P. H. DAVIS - Small-Flowered Oregano; found in Shoot
*Origanum onites* L. - Oregano, Pot Marjoram; found in Shoot
*Origanum vulgare* L. - Common Turkish Oregano, European Oregano, Oregano, Pot Marjoram, Wild Marjoram, Wild Oregano; found in Shoot
*Pelargonium graveolens* (L.) L'HER ex AIT. - Rose Geranium, Scented Geranium; found in Essential Oil
*Peumus boldus* MOLINA - Boldo; found in Leaf
*Pimenta dioica* (L.) MERR. - Allspice, Clover-Pepper, Jamaica-Pepper, Pimenta, Pimento; found in Fruit, Leaf
*Pimenta racemosa* (MILL.) J. W. MOORE - Bayrum Tree, West Indian Bay; found in Leaf
*Pimpinella anisum* L. - Anise, Sweet Cumin; found in Plant
*Piper betel* L. - Betel Pepper; found in Leaf
*Piper nigrum* L. - Black Pepper, Pepper, White Pepper; found in Fruit
*Pogostemon cablin* (BLANCO) BENTH. - Patchouli; found in Plant
*Polianthes tuberosa* L. - Tuberose; found in Flower
*Prunus cerasus* L. - Sour Cherry; found in Plant
*Prunus dulcis* (MILLER) D. A. WEBB - Almond; found in Flower
*Pycnanthemum setosum* NUTT. - Setose Mountain Mint; found in Shoot
*Rosa centifolia* L. - Cabbage Rose; found in Essential Oil
*Rosa damascena* MILLER - Damask Rose; found in Essential Oil
*Rosa gallica* L. - French Rose; found in Flower
*Santalum album* L. - White Sandalwood; found in Wood
*Sassafras albidum* (NUTT.) NEES - Sassafras; found in Root
*Syzygium aromaticum* (L.) MERR. & L. M. PERRY - Clove, Clovetree; found in Flower, Leaf, Stem
*Thymus capitatus* (L.) HOFFM. - 'Sicilian' Thyme, Spanish Origanum, Spanish Thyme; found in Shoot
*Thymus cilicicus* BOISS. & BAL. - 'Anatolian' Thyme; found in Shoot
*Thymus funkii* COUSS. - Funk's Thyme; found in Shoot
*Thymus vulgaris* L. - Common Thyme, Garden Thyme, Thyme; found in Plant
*Tilia* sp. - Basswood, Lime, Linden; found in Flower
*Trifolium pratense* L. - Cowgrass, Peavine Clover, Purple Clover, Red Clover; found in Flower
*Umbellularia californica* (HOOK. & ARN.) NUTT. - California Bay; found in Plant
*Vaccinium corymbosum* L. - Blueberry; found in Fruit
*Vaccinium macrocarpon* AITON - American Cranberry, Cranberry, Large Cranberry; found in Fruit
*Vanilla planifolia* JACKS. - Bourbon Vanilla, Vanilla; found in Fruit
*Viola odorata* L. - Common Violet, Sweet Violet; found in Flower, Leaf
*Zea mays* L. - Corn; found in Seed

1.8 KAEMPFEROL

*Abelmoschus moschatus* MEDIK. - Ambrette, Musk Okra, Muskmallow, Tropical Jewel Hibiscus; found in Flower
*Acacia catechu* (L. f.) WILLD. - Black Cutch, Catechu; found in Plant
*Acacia farnesiana* (L.) WILLD. - Cassie, Huisache, Opopanax, Popinac, Sweet Acacia; found in Plant
*Acacia senegal* (L.) WILLD. - Gum Arabic, Gum Arabic Tree, Kher, Senegal Gum, Sudan Gum Arabic; found in Plant
*Ageratum conyzoides* L. - Mexican ageratum; found in Plant
*Allium cepa* L. - Onion, Shallot; found in Bulb
*Allium sativum* var. *sativum* L. - Garlic; found in Plant
*Allium schoenoprasum* L. - Chives; found in Leaf
*Althaea officinalis* L. - Marshmallow, White Mallow; found in Leaf
*Ammi visnaga* (L.) LAM. - Visnaga; found in Plant
*Anethum graveolens* L. - Dill, Garden Dill; found in Fruit
*Armoracia rusticana* GAERTN. ET AL. - Horseradish; found in Leaf
*Asparagus officinalis* L. - Asparagus; found in Root
*Azadirachta indica* A. JUSS. - Neem; found in Flower
*Berberis vulgaris* L. - Barberry; found in Plant
*Beta vulgaris* subsp. subsp. *vulgaris* - Beet, Beetroot, Garden Beet, Sugar Beet; found in Plant
*Brassica oleracea* var. *botrytis* l. var. *botrytis* L. - Cauliflower; found in Flower, Leaf
*Brassica oleracea* var. *capitata* l. var. *capitata* L. - Cabbage, Red Cabbage, White Cabbage; found in Leaf
*Brassica oleracea* var. *gongylodes* L. - Kohlrabi; found in Shoot
*Brassica oleracea* var. *sabellica* l. var. *acephala* DC - Curly Kale, Kale, Kitchen Kale, Scotch Kale; found in Leaf
*Calendula officinalis* L. - Calendula, Pot-Marigold; found in Plant
*Camellia sinensis* (L.) KUNTZE - Tea; found in Plant
*Capsicum frutescens* L. - Cayenne, Chili, Hot Pepper, Red Chili, Spur Pepper, Tabasco; found in Anther
*Castanea sativa* MILLER - European Chestnut; found in Leaf
*Catharanthus roseus* (L.) G. DON - Madagascar Periwinkle, Rosy Periwinkle; found in Plant
*Ceiba pentandra* (L.) GAERTN. - Kapok, Silk-Cotton Tree; found in Flower
*Centella asiatica* (L.) URBAN - Gotu Kola, Pennywort; found in Plant

TABLE 1-continued

*Chimaphila umbellata* (L.) NUTT. - King's Cure, Pipsissewa; found in Plant
*Cichorium intybus* L. - Chicory, Succory, Witloof; found in Plant
*Cinnamomum camphora* (L.) NEES & EBERM. - Camphor, Ho Leaf; found in Plant
*Citrus paradisi* MacFAD. - Grapefruit; found in Fruit
*Cola acuminata* (P. BEAUV.) SCHOTT & ENDL. - Abata Cola; found in Plant
*Consolida ajacis* (L.) SCHUR - Larkspur; found in Flower
*Cornus florida* L. - American Dogwood; found in Flower
*Crocus sativus* L. - Saffron; found in Flower
*Cucurbita pepo* L. - Pumpkin; found in Leaf
*Cuscuta reflexa* ROXB. - Amarbel; found in Plant
*Daucus carota* L. - Carrot; found in Seed
*Diospyros virginiana* L. - American Persimmon; found in Plant
*Dodonaea viscosa* (L.) JACQ. - Hopwood; found in Plant
*Drimys winteri* FORSTER & FORSTER f. - Winter's Bark; found in Leaf
*Echinacea* spp - Coneflower, *Echinacea*; found in Leaf
*Elaeagnus angustifolia* L. - Russian Olive, Silver Berry; found in Leaf
*Equisetum arvense* L. - Field Horsetail, Horsetail; found in Plant
*Eriobotrya japonica* (THUNB.) LINDL. - Loquat; found in Plant
*Erythroxylum coca* var. *coca* - Coca; found in Plant
*Eupatorium perfoliatum* L. - Boneset; found in Plant
*Euphorbia hirta* L. - Queensland Asthma Herb; found in Leaf
*Euphorbia lathyris* L. - Caper Spurge, Mole Plant; found in Leaf
*Ficus carica* L. - Echte Feige (Ger.), Feigenbaum (Ger.), Fico (Ital.), Fig, Figueira (Port.), Figuier Commun (Fr.), Higo (Sp.), Higuera Comun (Sp.); found in Plant
*Foeniculum vulgare* MILLER - Fennel; found in Plant
*Fragaria* spp - Strawberry; found in Leaf
*Frangula alnus* MILLER - Buckthorn; found in Seed
*Geranium thunbergii* SIEB. & ZUCC - Gennoshiouko, Oriental Geranium; found in Leaf
*Ginkgo biloba* L. - *Ginkgo*, Maidenhair Tree; found in Leaf
*Glycine max* (L.) MERR. - Soybean; found in Plant
*Glycyrrhiza glabra* L. - Commom Licorice, Licorice, Licorice-Root, Smooth Licorice; found in Shoot
*Gossypium* sp - Cotton; found in Flower
*Hamamelis virginiana* L. - Witch Hazel; found in Leaf
*Harpagophytum procumbens* (BURCH.) DC. EX MEISN. - Devil's Claw, Grapple Plant; found in Root
*Hippophae rhamnoides* L. - Sallow Thorn, Sea Buckthorn, Yellow Spine; found in Fruit
*Humulus lupulus* L. - Hops; found in Leaf
*Hura crepitans* L. - Sandbox Tree; found in Leaf
*Hydrangea arborescens* L. - *Hydrangea*, Smooth *Hydrangea*; found in Root
*Isatis tinctoria* L. - Dyer's Woad; found in Plant
*Juglans regia* L. - English Walnut; found in Leaf
*Kalanchoe pinnata* (LAM.) PERS. - Air Plant, Siempre Viva; found in Leaf
*Kalanchoe spathulata* DC. - Beach Bells; found in Leaf
*Lactuca sativa* L. - Lettuce; found in Plant
*Laurus nobilis* L. - Bay, Bay Laurel, Bayleaf, Grecian Laurel, Laurel, Sweet Bay; found in Plant
*Ligustrum japonicum* THUNB. - Japanese Privet, Ligustri Fructus; found in Flower
*Lycopersicon esculentum* MILLER - Tomato; found in Seed
*Magnolia denudata* DESR. - Hsin-I, Xin-Yi; found in Plant
*Magnolia kobus* DC. - Hsin-I, Xin-Yi; found in Plant
*Magnolia officinalis* REHDER & E. H. WILSON - Chinese *Magnolia*, Hou Pu, *Magnolia*-Bark; found in Plant
*Mangifera indica* L. - Mango; found in Plant
*Matricaria recutita* L. - Annual Camomile, German Camomile, Wild Camomile; found in Plant
*Melaleuca leucadendra* (L.) L. - Cajeput; found in Plant
*Melia azedarach* L. - Chinaberry; found in Plant
*Moringa oleifera* LAM. - Ben Nut, Benzolive Tree, Drumstick Tree, Horseradish Tree, Jacinto (Sp.), Moringa, West Indian Ben; found in Flower
*Morus alba* L. - Sang-Pai-Pi, White Mulberry; found in Wood
*Musa x paradisiaca* L. - Banana, Plantain; found in Fruit, Plant
*Myristica fragrans* HOUTT. - Mace, Muskatnussbaum (Ger.), Nutmeg, nogal moscado (Sp.), nuez moscada (Sp.); found in Plant
*Nelumbo nucifera* L. - Water Lotus; found in Plant
*Nicotiana tabacum* L. - Tobacco; found in Leaf
*Ocimum basilicum* L. - Basil, Cuban Basil, Sweet Basil; found in Leaf
*Oenothera biennis* L. - Evening-Primrose; found in Leaf
*Olea europaea* subsp. *europaea* - Olive; found in Stem
*Opuntia ficus-indica* (L.) MILL. - Indian Fig, Nopal, Nopalito, Prickly Pear; found in Flower
*Origanum vulgare* L. - Common Turkish Oregano, European Oregano, Oregano, Pot Marjoram, Wild Marjoram, Wild Oregano; found in Plant
*Paeonia lactiflora* PALL. - Bai Shao (Chinese), Chih-Shao, Common Garden Peony, Peony, White Peony; found in Leaf
*Paeonia moutan* - Moutan, Tree Peony; found in Leaf
*Paeonia suffruticosa* ANDREWS - Moutan, Moutan Peony, Tree Peony; found in TABLE 1-continued Leaf
*Panax ginseng* C. A. MEYER - Chinese *Ginseng*, *Ginseng*, Korean *Ginseng*,
Oriental *Ginseng*; found in Leaf
*Panax quinquefolius* L. - American *Ginseng*, *Ginseng*; found in Plant
*Passiflora incarnata* L. - Manzana de Mayo, Mayapple, Passionflower; found in Plant
*Pastinaca sativa* L. - Parsnip; found in Seed
*Petasites japonicus* (SIEBOLD & ZUCC.) MAXIM. - Butterbur; found in Plant
*Petroselinum crispum* (MILLER) NYMAN EX A. W. HILLL - Parsley; found in
Plant
*Phyllanthus emblica* L. - Emblic, Myrobalan; found in Leaf
*Physalis peruviana* L. - Cape Gooseberry, Ground Cherry; found in Fruit
*Pinus mugo* TURRA - Dwarf Pine, Swiss Mountain Pine; found in Wood
*Pistacia lentiscus* L. - Chios Mastictree, Lentisco (Sp.), Mastic, Mastictree,
Mastixbaum (Ger.); found in Leaf
*Pisum sativum* L. - Pea; found in Tissue Culture
*Plumeria acutifolia* POIR. - Frangipani; found in Flower
*Podophyllum hexandrum* ROYLE - Himalayan Mayapple; found in Rhizome
*Podophyllum peltatum* L. - Mayapple; found in Rhizome
*Podophyllum pleianthum* L. - Chinese Mayapple; found in Rhizome
*Polygonum hydropiper* L. - Common Smartweed; found in Plant
*Polygonum hydropiperoides* L. - Mild Water Pepper; found in Plant
*Populus tacamahacca* MILL. - Balm Of Gilead; found in Plant
*Prunus armeniaca* L. - Apricot; found in Leaf
*Prunus cerasus* L. - Sour Cherry; found in Plant
*Prunus domestica* L. - Plum; found in Wood
*Prunus dulcis* (MILLER) D. A. WEBB - Almond; found in Plant
*Prunus laurocerasus* L. - Cherry Laurel; found in Plant
*Prunus persica* (L.) BATSCH - Peach; found in Leaf
*Prunus serotina* subsp. *serotina* - Black Cherry, Wild Cherry; found in Plant
*Prunus spinosa* L. - Blackthorn, Sloe; found in Flower
*Psidium cattleianum* SABINE - Strawberry Guava; found in Plant
*Rhododendron dauricum* L. - Chinese Alpenrose; found in Plant
*Rhus toxicodendron* L. - Poison Ivy; found in Plant
*Ribes nigrum* L. - Black Currant; found in Fruit
*Ricinus communis* L. - Castorbean; found in Plant
*Robinia pseudoacacia* L. - Black Locust; found in Flower
*Rosa damascena* MILLER - Damask Rose; found in Plant
*Sambucus nigra* L. - Black Elder, Elder, European Alder, European Elder, European
Elderberry; found in Flower
*Sanguisorba minor* SCOP. - Small Burnet; found in Plant
*Sanguisorba officinalis* L. - Greater Burnet; found in Plant
*Schinus molle* L. - California Peppertree, Mastic-Tree, Peruvian Peppertree; found in
Leaf
*Schinus terebinthifolius* RADDI - Brazilian Peppertree; found in Leaf
*Silybum marianum* (L.) GAERTN. - Lady's Thistle, Milk Thistle; found in Seed
*Solanum tuberosum* L. - Potato; found in Flower
*Sophora japonica* L. - Japanese Pagoda Tree; found in Plant
*Spinacia oleracea* L. - Spinach; found in Plant
*Syzygium aromaticum* (L.) MERR. & L. M. PERRY - Clove, Clovetree; found in
Flower
*Tagetes erecta* L. - Aztec Marigold, Marigold; found in Leaf
*Tagetes patula* L. - French Marigold; found in Plant
*Terminalia catappa* L. - Indian Almond, Malabar Almond, Tropical Almond; found
in Leaf
*Teucrium polium* L. - Golden Germander; found in Plant
*Theobroma cacao* L. - *Cacao*; found in Leaf
*Thespesia populnea* (L.) SOLAND. - Indian tulip tree; found in Flower
*Thevetia peruviana* (PERS.) K. SCHUM. - Adelfa Amarilla (Sp.), Cabalonga (Sp.),
Chirca (Sp.), Loandro-Amarelo (Port.), Luckynut, Oleandre Jaune (Fr.), Peruvian
Yellow Oleander, Thevetie (Ger.), Yellow Oleander; found in Plant
*Thymus vulgaris* L. - Common Thyme, Garden Thyme, Thyme; found in Plant
*Tribulus terrestris* L. - Puncture-vine; found in Flower
*Trigonella foenum-graecum* L. - Alholva (Sp.), Bockshornklee (Ger.), Fenugreek,
Greek Clover, Greek Hay; found in Plant
*Tsuga canadensis* (L.) CARRIERE - Eastern Hemlock; found in Branches
*Vaccinium vitis-idaea* var. *minus* LODD. - Cowberry, Lingen, Lingonberry; found in
Fruit
*Valeriana officinalis* L. - Common Valerian, Garden-Heliotrope, Valerian; found in
Plant
*Vicia faba* L. - Broadbean, Faba Bean, Habas; found in Shoot
*Viola odorata* L. - Common Violet, Sweet Violet; found in Plant
*Vitis vinifera* L. - European Grape, Grape, Grapevine, Parra (Sp.), Vid (Sp.), Vigne
Vinifere (Fr.), Weinrebe (Ger.), Wine Grape; found in Leaf
*Zingiber officinale* ROSCOE - Ginger; found in Plant 1.9 OLEANDIC ACID

*Achyranthes aspera* BLUME - Chaff Flower; found in Plant
*Achyranthes bidentata* BLUME - Chaff Flower; found in Fruit
*Akebia quinata* (THUNB.) DECNE - Chocolate Vine; found in Stem

TABLE 1-continued

*Allium cepa* L. - Onion, Shallot; found in Bulb
*Allium sativum* var. *sativum* L. - Garlic; found in Plant
*Apocynum cannabinum* L. - Bitterroot, Spreading Dogbane; found in Root
*Arctostaphylos uva-ursi* (L.) SPRENGEL - Bearberry, *Uva Ursi*; found in Plant
*Calendula officinalis* L. - Calendula, Pot-Marigold; found in Flower
*Catharanthus roseus* (L.) G. DON - Madagascar Periwinkle, Rosy Periwinkle; found in Plant
*Centaurium erythraea* RAFN. - Centaury; found in Plant
*Chenopodium album* L. - Lambsquarter; found in Plant
*Citrullus colocynthis* - Colocynth; found in Plant
*Cnicus benedictus* L. - Blessed Thistle; found in Plant
*Cornus officinalis* SIEB. & ZUCC. - Chinese Dogwood; found in Seed
*Cyperus rotundus* L. - Nutsedge; found in Tuber
*Daemonorops draco* BL. - Dragon's Blood; found in Fruit
*Elaeagnus pungens* THUNB. - Thorny Silver Berry; found in Leaf
*Eleutherococcus senticosus* (RUPR. & MAXIM.) MAXIM. - Ci wu jia (Pinyin), Eleuthero *Ginseng*, Siberian *Ginseng*, Spiny *Ginseng*, Wu jia; found in Root
*Eriobotrya japonica* (THUNB.) LINDL. - Loquat; found in Leaf
*Forsythia suspensa* VAHL - Lian-Jiao, Lien-Chiao; found in Fruit
*Glechoma hederacea* L. - Alehoof; found in Plant
*Harpagophytum procumbens* (BURCH.) DC. EX MEISN. - Devil's Claw, Grapple Plant; found in Root
*Hedera helix* L. - Ivy; found in Leaf
*Helianthus annuus* L. - Girasol, Sunflower; found in Flower
*Humulus lupulus* L. - Hops; found in Stem
*Hyssopus officinalis* L. - Hyssop; found in Plant
*Lavandula latifolia* MEDIK. - Aspic, Broad-Leaved Lavender, Spike Lavender; found in Leaf
*Leonurus cardiaca* L. - Motherwort; found in Plant
*Ligustrum japonicum* THUNB. - Japanese Privet, Ligustri Fructus; found in Fruit
*Ligustrum lucidum* W. T. AITON - Chinese Privet, Glossy Privet, Ligustri Fructus, Privet, White Waxtree; found in Fruit
*Liquidambar orientalis* MILLER - Oriental Storax, Oriental Styrax; found in Resin, Exudate, Sap
*Liquidambar styraciflua* L. - American Styrax, Sweetgum; found in Resin, Exudate, Sap
*Luffa aegyptiaca* MILLER - *Luffa*, Smooth Loofah, Vegetable Sponge; found in Seed
*Melaleuca leucadendra* (L.) L. - Cajeput; found in Plant
*Melissa officinalis* L. - Balm, Bee Balm, Lemonbalm, Melissa; found in Shoot
*Mentha spicata* L. - Hortela da Folha Miuda, Spearmint; found in Leaf
*Mentha x rotundifolia* (L.) HUDSON - Applemint; found in Tissue Culture
*Myristica fragrans* HOUTT. - Mace, Muskatnussbaum (Ger.), Nutmeg, nogal moscado (Sp.), nuez moscada (Sp.); found in Seed
*Myroxylon balsamum* (L.) HARMS - Peru Balsam, Tolu Balsam; found in Plant
*Nerium oleander* L. - Oleander; found in Plant
*Ocimum basilicum* L. - Basil, Cuban Basil, Sweet Basil; found in Flower
*Ocimum suave* WILLD. - Kenyan Tree Basil; found in Leaf
*Olea europaea* subsp. *europaea* - Olive; found in Petiole
*Origanum majorana* L. - Marjoram, Sweet Marjoram; found in Plant
*Origanum vulgare* L. - Common Turkish Oregano, European Oregano, Oregano, Pot Marjoram, Wild Marjoram, Wild Oregano; found in Plant
*Panax ginseng* C. A. MEYER - Chinese *Ginseng*, *Ginseng*, Korean *Ginseng*, Oriental *Ginseng*; found in Root
*Panax japonicus* C. A. MEYER - Japanese *Ginseng*; found in Rhizome
*Panax quinquefolius* L. - American *Ginseng*, *Ginseng*; found in Plant
*Phytolacca americana* L. - Pokeweed; found in Root
*Plantago major* L. - Common Plantain; found in Leaf
*Plectranthus amboinicus* (LOUR.) SPRENGEL - Amboini Coleus, Country Borage, Cuban Oregano, French Thyme, Indian Borage, Mexican Mint, Soup Mint, Spanish Thyme; found in Plant
*Prunella vulgaris* L. - Heal-All, Self-Heal; found in Plant
*Prunus cerasus* L. - Sour Cherry; found in Fruit
*Psidium guajava* L. - Guava; found in Leaf
*Quisqualis indica* L. - Rangoon Creeper; found in Fruit
*Rosmarinus officinalis* L. - Rosemary; found in Plant, Shoot
*Salvia officinalis* L. - Sage; found in Leaf, Stem
*Salvia sclarea* L. - Clary Sage; found in Plant
*Salvia triloba* L. - Greek Sage; found in Plant
*Sambucus nigra* L. - Black Elder, Elder, European Alder, European Elder, European Elderberry; found in Bark, Leaf
*Satureja hortensis* L. - Summer Savory; found in Plant
*Satureja montana* L. - Savory, Winter Savory; found in Plant
*Syzygium aromaticum* (L.) MERR. & L. M. PERRY - Clove, Clovetree; found in Flower
*Thymus serpyllum* L. - Creeping Thyme; found in Plant
*Thymus vulgaris* L. - Common Thyme, Garden Thyme, Thyme; found in Plant
*Uncaria tomentosa* DC - Cat's Claw, Garabato Amarillo, Una de Gato; found in TABLE 1-continued Plant
*Vaccinium corymbosum* L. - Blueberry; found in Plant
*Vaccinium myrtillus* L. - Bilberry, Dwarf Bilberry, Whortleberry; found in Leaf
*Viburnum prunifolium* L. - Black Haw; found in Bark
*Viscum album* L. - European Mistletoe; found in Resin, Exudate, Sap
*Vitis vinifera* L. - European Grape, Grape, Grapevine, Parra (Sp.), Vid (Sp.), Vigne Vinifere (Fr.), Weinrebe (Ger.), Wine Grape; found in Leaf Wax
*Zizyphus jujuba* MILL. - Da-Zao, Jujube, Ta-Tsao; found in Plant 1.10 QUERCETIN

*Abelmoschus esculentus* (L.) MOENCH - Okra; found in Flower
*Abelmoschus moschatus* MEDIK. - Ambrette, Musk Okra, Muskmallow, Tropical Jewel Hibiscus; found in Flower
*Acacia catechu* (L. f.) WILLD. - Black Cutch, *Catechu*; found in Plant
*Acacia nilotica* (L.) WILLD. ex DELILE - Babul; found in Plant
*Acacia senegal* (L.) WILLD. - Gum Arabic, Gum Arabic Tree, Kher, Senegal Gum, Sudan Gum Arabic; found in Plant
*Achillea millefolium* L. - Milfoil, Yarrow; found in Plant
*Actinidia chinensis* PLANCHON - Kiwi; found in Plant
*Aesculus hippocastanum* L. - Horse Chestnut; found in Bark
*Agathosma betulina* (P. J. BERGIUS) PILLANS - Buchu, Honey Buchu, Mountain Buchu; found in Plant
*Ageratum conyzoides* L. - Mexican ageratum; found in Plant
*Ailanthus altissima* (MILL.) SWINGLE - Stinktree, Tree Of Heaven; found in Leaf
*Allium cepa* L. - Onion, Shallot; found in Bulb
*Allium sativum* var. *sativum* L. - Garlic; found in Bulb
*Allium schoenoprasum* L. - Chives; found in Leaf
*Althaea officinalis* L. - Marshmallow, White Mallow; found in Leaf
*Ammi majus* L. - Bishop's Weed; found in Leaf
*Ammi visnaga* (L.) LAM. - Visnaga; found in Plant
*Anastatica hierochuntica* L. - Jericho Rose; found in Plant
*Anethum graveolens* L. - Dill, Garden Dill; found in Plant
*Anogeissus latifolia* WALL. - Gum Ghatti; found in Plant
*Arachis hypogaea* L. - Groundnut, Peanut; found in Plant
*Araucaria bidwillii* HOOK. - Monkey puzzle; found in Flower
*Arctostaphylos uva-ursi* (L.) SPRENGEL - Bearberry, Uva Ursi; found in Leaf
*Ardisia japonica* L. - Marlberry; found in Plant
*Armoracia rusticana* GAERTN. ET AL. - Horseradish; found in Leaf
*Artemisia dracunculus* L. - Tarragon; found in Shoot
*Artocarpus altilis* (PARKINS.) FOSBERG - Breadfruit; found in Leaf
*Asimina triloba* (L.) DUNAL - Pawpaw; found in Leaf
*Asparagus officinalis* L. - Asparagus; found in Root
*Avena sativa* L. - Oats; found in Hay
*Azadirachta indica* A. JUSS. - Neem; found in Flower, Leaf
*Barosma betulina* (P. J. BERGIUS) BARTL. & H. L. WENDL. - Buchu; found in Plant
*Basella alba* L. - Vinespinach; found in Plant
*Berberis vulgaris* L. - Barberry; found in Plant
*Beta vulgaris* subsp. subsp. *vulgaris* - Beet, Beetroot, Garden Beet, Sugar Beet; found in Plant
*Brassica oleracea* var. *botrytis* 1. var. *botrytis* L. - Cauliflower; found in Flower, Leaf
*Brassica oleracea* var. *capitata* 1. var. *capitata* L. - Cabbage, Red Cabbage, White Cabbage; found in Leaf
*Brassica oleracea* var. *gemmifera* var. *gemmifera* DC - Brussel-Sprout, Brussels-Sprouts; found in Sprout Seedling
*Brassica oleracea* var. *gongylodes* L. - Kohlrabi; found in Shoot
*Brassica oleracea* var. *sabellica* 1. var. *acephala* DC - Curly Kale, Kale, Kitchen Kale, Scotch Kale; found in Leaf
*Caesalpinia pulcherrima* (L.) SW. - Bird Of Paradise; found in Flower
*Calendula officinalis* L. - *Calendula*, Pot-Marigold; found in Plant
*Camellia sinensis* (L.) KUNTZE - Tea; found in Leaf, Plant
*Camptotheca acuminata* DECAISNE - Happy Tree; found in Leaf
*Capparis spinosa* L. - Caper, Caperbush; found in Flower
*Capsicum frutescens* L. - Cayenne, Chili, Hot Pepper, Red Chili, Spur Pepper, Tabasco; found in Fruit
*Carum carvi* L. - Caraway, Carum, Comino (Sp.), Comino de prado (Sp.), Kummel (Ger.); found in Fruit
*Castanea sativa* MILLER - European Chestnut; found in Bark, Leaf, Wood
*Catharanthus roseus* (L.) G. DON - Madagascar Periwinkle, Rosy Periwinkle; found in Plant
*Cedrus deodora* LOUD. - Deodar Cedar; found in Stem Bark
*Ceiba pentandra* (L.) GAERTN. - Kapok, Silk-Cotton Tree; found in Leaf
*Centaurea calcitrapa* L. - Star-Thistle; found in Plant
*Cichorium endivia* L. - Endive, Escarole; found in Leaf
*Cichorium intybus* L. - Chicory, Succory, Witloof; found in Plant
*Cinnamomum camphora* (L.) NEES & EBERM. - Camphor, Ho Leaf; found in Plant
*Citrus limon* (L.) BURMAN f. - Lemon; found in Flower
*Citrus paradisi* MacFAD. - Grapefruit; found in Fruit
*Consolida ajacis* (L.) SCHUR - Larkspur; found in Flower

TABLE 1-continued

*Coriandrum sativum* L. - Chinese Parsley, Cilantro, Coriander; found in Fruit
*Coriaria myrtifolia* L. - Mealy Tree; found in Leaf
*Coriaria thymifolia* HUMB. & BONPL. - Ground Toot, Shanshi; found in Plant
*Cornus florida* L. - American Dogwood; found in Flower
*Crataegus cuneata* SIEB. & ZUCC. - Hawthorn; found in Fruit
*Crocus sativus* L. - Saffron; found in Flower
*Cucurbita pepo* L. - Pumpkin; found in Leaf
*Cymbopogon citratus* (DC. ex NEES) STAPF - Lemongrass, West Indian Lemongrass; found in Plant
*Cytisus scoparius* (L.) LINK. - Scotch Broom; found in Plant
*Daucus carota* L. - Carrot; found in Seed
*Diospyros virginiana* L. - American Persimmon; found in Plant
*Dodonaea viscosa* (L.) JACQ. - Hopwood; found in Plant
*Drimys winteri* FORSTER & FORSTER f. - Winter's Bark; found in Leaf
*Echinacea* spp - Coneflower, *Echinacea*; found in Leaf
*Elaeagnus angustifolia* L. - Russian Olive, Silver Berry; found in Leaf
*Eriobotrya japonica* (THUNB.) LINDL. - Loquat; found in Plant
*Eucalyptus globulus* LABILL. - Blue Gum, Eucalypt, Tasmanian Bluegum; found in Leaf
*Eupatorium perfoliatum* L. - Boneset; found in Plant
*Euphorbia hirta* L. - Queensland Asthma Herb; found in Plant
*Euphorbia lathyris* L. - Caper Spurge, Mole Plant; found in Leaf
*Fagopyrum esculentum* MOENCH. - Buckwheat; found in Plant
*Ficus carica* L. - Echte Feige (Ger.), Feigenbaum (Ger.), Fico (Ital.), Fig, Figueira (Port.), Figuier Commun (Fr.), Higo (Sp.), Higuera Comun (Sp.); found in Plant
*Filipendula ulmaria* (L.) MAXIM. - Meadowsweet, Queen Of The Meadow; found in Flower
*Foeniculum vulgare* MILLER - Fennel; found in Fruit
*Forsythia suspensa* VAHL - Lian-Jiao, Lien-Chiao; found in Flower
*Fragaria* spp - Strawberry; found in Leaf
*Geranium thunbergii* SIEB. & ZUCC - Gennoshiouko, Oriental Geranium; found in Leaf
*Ginkgo biloba* L. - *Ginkgo*, Maidenhair Tree; found in Leaf
*Glycine max* (L.) MERR. - Soybean; found in Plant
*Glycyrrhiza glabra* L. - Commom Licorice, Licorice, Licorice-Root, Smooth Licorice; found in Plant
*Gossypium* sp - Cotton; found in Plant
*Haematoxylum campechianum* L. - Campechy, Logwood; found in Leaf
*Hamamelis virginiana* L. - Witch Hazel; found in Leaf
*Helianthus annuus* L. - Girasol, Sunflower; found in Flower, Leaf
*Hibiscus rosa-sinensis* L. - Chinese hibiscus, Shoe-flower; found in Plant
*Hippophae rhamnoides* L. - Sallow Thorn, Sea Buckthorn, Yellow Spine; found in Fruit
*Houttuynia cordata* THUNB. - Dokudami, Fishwort, Yu Xing Cao; found in Plant
*Matricaria recutita* L. - Annual Camomile, German Camomile, Wild Camomile; found in Plant
*Melia azedarach* L. - Chinaberry; found in Plant
*Moringa oleifera* LAM. - Ben Nut, Benzolive Tree, Drumstick Tree, Horseradish Tree, Jacinto (Sp.), Moringa, West Indian Ben; found in Flower
*Morus alba* L. - Sang-Pai-Pi, White Mulberry; found in Plant
*Musa x paradisiaca* L. - Banana, Plantain; found in Fruit, Plant
*Myristica fragrans* HOUTT. - Mace, Muskatnussbaum (Ger.), Nutmeg, nogal moscado (Sp.), nuez moscada (Sp.); found in Plant
*Nelumbo nucifera* L. - Water Lotus; found in Flower
*Nerium oleander* L. - Oleander; found in Leaf
*Nicotiana tabacum* L. - Tobacco; found in Flower
*Ocimum basilicum* L. - Basil, Cuban Basil, Sweet Basil; found in Leaf
*Oenothera biennis* L. - Evening-Primrose; found in Herb, Leaf
*Olea europaea* subsp. *europaea* - Olive; found in Stem
*Origanum vulgare* L. - Common Turkish Oregano, European Oregano, Oregano, Pot Marjoram, Wild Marjoram, Wild Oregano; found in Plant
*Paeonia lactiflora* PALL. - Bai Shao (Chinese), Chih-Shao, Common Garden Peony, Peony, White Peony; found in Leaf
*Paeonia moutan* - Moutan, Tree Peony; found in Leaf
*Paeonia suffruticosa* ANDREWS - Moutan, Moutan Peony, Tree Peony; found in Leaf
*Panax notoginseng* (BURKILL) HOO & TSENG - Sanchi *Ginseng*; found in Root
*Passiflora incarnata* L. - Manzana de Mayo, Mayapple, Passionflower; found in Leaf
*Pastinaca sativa* L. - Parsnip; found in Leaf
*Perilla frutescens* (L.) BRITTON - *Perilla*; found in Leaf
*Persea americana* MILLER - Avocado; found in Leaf
*Petroselinum crispum* (MILLER) NYMAN EX A. W. HILLL - Parsley; found in Plant
*Phoenix dactylifera* L. - Date Palm; found in Pollen Or Spore
*Phyllanthus niruri* L. - Seed On The Leaf; found in Plant
*Pinus mugo* TURRA - Dwarf Pine, Swiss Mountain Pine; found in Wood
*Pinus sylvestris* L. - Scotch Pine; found in Bark
*Pistacia lentiscus* L. - Chios Mastictree, Lentisco (Sp.), Mastic, Mastictree, Mastixbaum (Ger.); found in Leaf

TABLE 1-continued

*Plumeria acutifolia* POIR. - Frangipani; found in Flower
*Podophyllum hexandrum* ROYLE - Himalayan Mayapple; found in Rhizome
*Podophyllum peltatum* L. - Mayapple; found in Resin, Exudate, Sap
*Podophyllum pleianthum* L. - Chinese Mayapple; found in Rhizome
*Polygonum aviculare* L. - Prostrate Knotweed; found in Plant
*Polygonum hydropiper* L. - Common Smartweed; found in Plant
*Polygonum hydropiperoides* L. - Mild Water Pepper; found in Plant
*Populus tacamahacca* MILL. - Balm Of Gilead; found in Plant
*Prosopis juliflora* (SW.) DC. - Mesquite; found in Plant
*Prunus armeniaca* L. - Apricot; found in Plant
*Prunus cerasus* L. - Sour Cherry; found in Fruit
*Prunus domestica* L. - Plum; found in Plant
*Prunus dulcis* (MILLER) D. A. WEBB - Almond; found in Plant
*Prunus laurocerasus* L. - Cherry Laurel; found in Plant
*Prunus persica* (L.) BATSCH - Peach; found in Plant
*Prunus serotina* subsp. *serotina* - Black Cherry, Wild Cherry; found in Plant
*Prunus spinosa* L. - Blackthorn, Sloe; found in Flower
*Psidium cattleianum* SABINE - Strawberry Guava; found in Plant
*Psidium guajava* L. - Guava; found in Leaf
*Pteridium aquilinum* (L.) KUHN - Bracken, Bracken Fern; found in Plant
*Pueraria montana* subsp. var. *lobata* (WILLD.) MAESEN & S. M. ALMEIDA-Kudsu, Kudzu; found in Leaf
*Pyrus communis* L. - Pear; found in Pericarp
*Quercus alba* L. - White Oak; found in Bark
*Quercus infectoria* OLIV. - Aleppo Oak, Dyer's Oak, Gall Oak; found in Leaf
*Quercus robur* L. - English Oak; found in Bark
*Quercus velutina* LAM. - Black Oak; found in Plant
*Rhododendron dauricum* L. - Chinese Alpenrose; found in Plant
*Rhus toxicodendron* L. - Poison Ivy; found in Plant
*Ribes nigrum* L. - Black Currant; found in Fruit
*Ricinus communis* L. - Castorbean; found in Plant
*Rosa damascena* MILLER - Damask Rose; found in Flower
*Rosa* spp - Rose Hips; found in Fruit
*Rumex acetosa* L. - Garden Sorrel; found in Fruit
*Rumex crispus* L. - Curly Dock, Lengua De Vaca, Sour Dock, Yellow Dock; found in Leaf
*Ruta graveolens* L. - Rue; found in Plant
*Salix alba* L. - White Willow; found in Bark
*Sambucus nigra* L. - Black Elder, Elder, European Alder, European Elder, European Elderberry; found in Leaf
*Sanguisorba minor* SCOP. - Small Burnet; found in Plant
*Sanguisorba officinalis* L. - Greater Burnet; found in Plant
*Schinus molle* L. - California Peppertree, Mastic-Tree, Peruvian Peppertree; found in Leaf
*Schinus terebinthifolius* RADDI - Brazilian Peppertree; found in Plant
*Senna occidentalis* (L.) H. IRWIN & BARNEBY - Coffee Senna; found in Root
*Silybum marianum* (L.) GAERTN. - Lady's Thistle, Milk Thistle; found in Seed
*Solanum tuberosum* L. - Potato; found in Flower
*Solidago virgaurea* L. - European Goldenrod, Woundwort; found in Leaf
*Sophora japonica* L. - Japanese Pagoda Tree; found in Plant
*Sorbus aucubaria* L. - Rowan Berry; found in Fruit
*Spartium junceum* L. - Genet, Spanish Broom, Weaver's Broom; found in Plant
*Spinacia oleracea* L. - Spinach; found in Leaf
*Tagetes patula* L. - French Marigold; found in Plant
*Tanacetum vulgare* L. - Tansy; found in Plant
*Terminalia catappa* L. - Indian Almond, Malabar Almond, Tropical Almond; found in Leaf
*Teucrium botrys* L. - Field Germander; found in Plant
*Teucrium montanum* L. - Mountain Germander; found in Plant
*Teucrium scordium* - Water Germander; found in Plant
*Theobroma cacao* L. - *Cacao*; found in Leaf
*Thespesia populnea* (L.) SOLAND. - Indian tulip tree; found in Flower
*Thevetia peruviana* (PERS.) K. SCHUM. - Adelfa Amarilla (Sp.), Cabalonga (Sp.), Chirca (Sp.), Loandro-Amarelo (Port.), Luckynut, Oleandre Jaune (Fr.), Peruvian Yellow Oleander, Thevetie (Ger.), Yellow Oleander; found in Plant
*Tilia* sp. - Basswood, Lime, Linden; found in Flower
*Tribulus terrestris* L. - Puncture-vine; found in Flower
*Tridax procumbens* L. - Coatbuttons, Mexican daisy; found in Flower
*Trigonella foenum-graecum* L. - Alholva (Sp.), Bockshornklee (Ger.), Fenugreek, Greek Clover, Greek Hay; found in Seed
*Triticum aestivum* L. - Wheat; found in Plant
*Tussilago farfara* L. - Coltsfoot; found in Leaf
*Uncaria catechu* (L. f.) WILLD. - Gambir, Pale *Catechu*; found in Bulb
*Urginea maritima* L. - European Squill; found in Bulb
*Vaccinium corymbosum* L. - Blueberry; found in Plant
*Vaccinium macrocarpon* AITON - American Cranberry, Cranberry, Large Cranberry; found in Fruit
*Vaccinium myrtillus* L. - Bilberry, Dwarf Bilberry, Whortleberry; found in Leaf
*Vaccinium vitis-idaea* var. *minus* LODD. - Cowberry, Lingen, Lingonberry; found in TABLE 1-continued Leaf
*Valeriana officinalis* L. - Common Valerian, Garden-Heliotrope, Valerian; found in Plant
*Viola odorata* L. - Common Violet, Sweet Violet; found in Plant
*Viola tricolor* L. - Pansy, Wild Violet; found in Flower
*Vitis vinifera* L. - European Grape, Grape, Grapevine, Parra (Sp.), Vid (Sp.), Vigne Vinifere (Fr.), Weinrebe (Ger.), Wine Grape; found in Fruit
*Zea mays* L. - Corn; found in Plant
*Zingiber officinale* ROSCOE - Ginger; found in Plant 1.11 RESVERATROL

*Morus alba* L. - Sang-Pai-Pi, White Mulberry; found in Wood
*Polygonum cuspidatum* SIEBOLD & ZUCC. - Giant Knotweed, Hu-Zhang, Japanese Knotweed, Mexican Bamboo; found in Root
*Vitis vinifera* L. - European Grape, Grape, Grapevine, Parra (Sp.), Vid (Sp.), Vigne Vinifere (Fr.), Weinrebe (Ger.), Wine Grape; found in Leaf
Trans-Resveratrol:
*Arachis hypogaea* L. - Groundnut, Peanut; found in Sprout Seedling 1.12 SALICYLIC ACID

*Abies alba* MILLER - Silver-Fir; found in Plant
*Acacia farnesiana* (L.) WILLD. - Cassie, Huisache, Opopanax, Popinac, Sweet Acacia ; found in Plant
*Achillea millefolium* L. - Milfoil, Yarrow; found in Plant
*Althaea officinalis* L. - Marshmallow, White Mallow; found in Leaf
*Anacardium occidentale* L. - Cashew; found in Fruit
*Arachis hypogaea* L. - Groundnut, Peanut; found in Seed
*Artemisia absinthium* L. - Wormwood; found in Plant
*Artemisia dracunculus* L. - Tarragon; found in Leaf
*Beta vulgaris* subsp. subsp. *vulgaris* - Beet, Beetroot, Garden Beet, Sugar Beet; found in Root
*Bixa orellana* L. - Achiote, Annato, Annatto, Annoto, Arnato, Bija, Lipstick Pod, Lipsticktree; found in Plant
*Brassica oleracea* var. *botrytis* L. var. *botrytis* L. - Cauliflower; found in Leaf
*Calea zacatechichi* SCHLECHT. - Bitter Grass, Dog's Grass, Mexican Calea; found in Plant
*Calendula officinalis* L. - Calendula, Pot-Marigold; found in Plant
*Camellia sinensis* (L.) KUNTZE - Tea; found in Leaf
*Cananga odorata* (LAM.) HOOK. f. & THOMSON - Cananga, Ylang-Ylang; found in Flower
*Cimicifuga racemosa* (L.) NUTT. - Black Cohosh, Black Snakeroot; found in Plant
*Cinnamomum aromaticum* NEES - Canela de la China (Sp.), Canelero chino (Sp.), Canelle de Cochinchine (Fr.), Cannelier Casse (Fr.), Cannelier de Chine (Fr.), Cassia, Cassia Bark, Cassia Lignea, China Junk Cassia, Chinazimt (Ger.), Chinese Cassia, Chinese Cinnamon, Chinesischer Zimtbaum (Ger.), Kashia-Keihi (Jap.), Saigon Cinnamon, Zimtcassie (Ger.); found in Plant
*Colchicum autumnale* L. - Autumn Crocus, Meadow Saffron; found in Plant
*Cucurbita pepo* L. - Pumpkin; found in Seed
*Dipteryx odorata* (AUBL.) WILLD. - Dutch Tonka Bean, Tonka Bean; found in Leaf
*Filipendula ulmaria* (L.) MAXIM. - Meadowsweet, Queen Of The Meadow; found in Flower
*Fragaria* spp - Strawberry; found in Fruit
*Gloriosa superba* L. - Glory Lily; found in Bulb
*Glycine max* (L.) MERR. - Soybean; found in Seed
*Glycyrrhiza glabra* L. - Commom Licorice, Licorice, Licorice-Root, Smooth Licorice; found in Root
*Gossypium* sp - Cotton; found in Root
*Hedeoma pulegioides* (L.) PERS. - American Pennyroyal; found in Plant
*Iris versicolor* L. - Blue Flag; found in Rhizome
*Jasminum officinale* L. - Jasmine, Poet's Jessamine; found in Leaf
*Matricaria recutita* L. - Annual Camomile, German Camomile, Wild Camomile; found in Plant
*Mentha pulegium* L. - European Pennyroyal; found in Essential Oil
*Panax quinquefolius* L. - American *Ginseng, Ginseng*; found in Plant
*Pisum sativum* L. - Pea; found in Plant
*Plantago major* L. - Common Plantain; found in Plant
*Polygonum aviculare* L. - Prostrate Knotweed; found in Plant
*Polypodium vulgare* L. - Common Polypody, Sweet Fern; found in Leaf
*Ribes rubrum* L. - Red Currant, White Currant; found in Fruit
*Rosa multiflora* THUNB. ex MURRAY - Multiflora Rose; found in Fruit
*Rubus idaeus* L. - Raspberry, Red Raspberry; found in Fruit
*Salix alba* L. - White Willow; found in Plant
*Salvia officinalis* L. - Sage; found in Plant
*Stachytarpheta cayennensis* VAHL - Verbena; found in Plant
*Trifolium pratense* L. - Cowgrass, Peavine Clover, Purple Clover, Red Clover; found in Flower
*Triticum aestivum* L. - Wheat; found in Seed
*Vaccinium vitis-idaea* var. *minus* LODD. - Cowberry, Lingen, Lingonberry; found in TABLE 1-continued Fruit
*Viburnum prunifolium* L. - Black Haw; found in Bark
*Viola odorata* L. - Common Violet, Sweet Violet; found in Leaf
*Viola tricolor* L. - Pansy, Wild Violet; found in Flower
*Vitis vinifera* L. - European Grape, Grape, Grapevine, Parra (Sp.), Vid (Sp.), Vigne Vinifere (Fr.), Weinrebe (Ger.), Wine Grape; found in Root 1.13 URSOLINIC-ACID

*Agrimonia eupatoria* L. - Agrimony, Sticklewort; found in Plant
*Arbutus unedo* L. - Arbutus, Strawberry Tree; found in Leaf
*Arctostaphylos uva-ursi* (L.) SPRENGEL - Bearberry, Uva Ursi; found in Leaf
*Artocarpus heterophyllus* LAM. - Jackfruit; found in Root
*Catalpa bignonioides* WALT. - Indian bean; found in Leaf
*Catharanthus roseus* (L.) G. DON - Madagascar Periwinkle, Rosy Periwinkle; found in Leaf
*Chimaphila umbellata* (L.) NUTT. - King's Cure, Pipsissewa; found in Plant
*Cornus florida* L. - American Dogwood; found in Plant
*Cornus officinalis* SIEB. & ZUCC. - Chinese Dogwood; found in Fruit, Seed
*Crataegus cuneata* SIEB. & ZUCC. - Hawthorn; found in Fruit
*Crataegus laevigata* (POIR.) DC - English Hawthorn, Hawthorn, Whitethorn, Woodland Hawthorn; found in Leaf
*Cryptostegia grandifolia* R. BR. - Rubber Vine; found in Leaf
*Elaeagnus pungens* THUNB. - Thorny Silver Berry; found in Leaf
*Eriobotrya japonica* (THUNB.) LINDL. - Loquat; found in Leaf
*Eucalyptus citriodora* HOOK. - Citron-Scented Gum, Lemon Eucalyptus, Lemon-Scented Gum, Spotted Gum; found in Plant
*Forsythia suspensa* VAHL - Lian-Jiao, Lien-Chiao; found in Fruit
*Gaultheria fragrantissima* WALL. - Indian Wintergreen; found in Leaf
*Glechoma hederacea* L. - Alehoof; found in Plant
*Helichrysum angustifolium* DC. - Everlasting, Immortelle; found in Flower, Stem
*Humulus lupulus* L. - Hops; found in Stem
*Hyssopus officinalis* L. - Hyssop; found in Plant
*Ilex paraguariensis* ST. HIL. - Mate, Paraguay Tea, South American Holly; found in Leaf
*Lavandula angustifolia* MILLER - English Lavender; found in Leaf
*Lavandula latifolia* MEDIK. - Aspic, Broad-Leaved Lavender, Spike Lavender; found in Leaf
*Leonurus cardiaca* L. - Motherwort; found in Plant
*Ligustrum japonicum* THUNB. - Japanese Privet, Ligustri Fructus; found in Fruit
*Limonia acidissima* L. - Elephant Apple, Manzana De Elefante, Wood-Apple; found in Wood
*Lycopus europeus* L. - European Bugle; found in Plant
*Malus domestica* BORKH. - Apple; found in Fruit Epidermis
*Marrubium vulgare* L. - Horehound, White Horehound; found in Plant
*Melaleuca leucadendra* (L.) L. - Cajeput; found in Plant
*Melissa officinalis* L. - Balm, Bee Balm, Lemonbalm, Melissa; found in Plant
*Mentha spicata* L. - Hortela da Folha Miuda, Spearmint; found in Leaf
*Mentha x rotundifolia* (L.) HUDSON - Applemint; found in Tissue Culture
*Monarda didyma* L. - Beebalm, Oswego Tea; found in Leaf
*Nerium oleander* L. - Oleander; found in Plant
*Ocimum basilicum* L. - Basil, Cuban Basil, Sweet Basil; found in Flower, Leaf, Sprout Seedling, Stem
*Ocimum canum* SIMS - Hoary Basil; found in Shoot
*Origanum majorana* L. - Marjoram, Sweet Marjoram; found in Plant
*Origanum vulgare* L. - Common Turkish Oregano, European Oregano, Oregano, Pot Marjoram, Wild Marjoram, Wild Oregano; found in Plant
*Plantago asiatica* L. - Asian Plantain; found in Plant
*Plantago major* L. - Common Plantain; found in Plant
*Plectranthus amboinicus* (LOUR.) SPRENGEL - Amboini Coleus, Country Borage, Cuban Oregano, French Thyme, Indian Borage, Mexican Mint, Soup Mint, Spanish Thyme; found in Plant
*Prunella vulgaris* L. - Heal-All, Self-Heal; found in Plant
*Prunus cerasus* L. - Sour Cherry; found in Fruit
*Prunus laurocerasus* L. - Cherry Laurel; found in Leaf
*Prunus persica* (L.) BATSCH - Peach; found in Leaf
*Prunus serotina* subsp. *serotina* - Black Cherry, Wild Cherry; found in Leaf
*Psidium guajava* L. - Guava; found in Leaf
*Punica granatum* L. - Granado (Sp.), Granatapfelbaum (Ger.), Granatapfelstrauch (Ger.), Grenadier (Fr.), Mangrano (Sp.), Pomegranate, Romanzeiro (Port.), Zakuro (Jap.); found in Fruit, Leaf
*Pyrus communis* L. - Pear; found in Fruit
*Rhododendron dauricum* L. - Chinese Alpenrose; found in Plant
*Rhododendron ferrugineum* L. - Rusty-Leaved Alpenrose; found in Leaf
*Rhododendron ponticum* L. - Pontic Alpenrose; found in Leaf
*Rosmarinus officinalis* L. - Rosemary; found in Plant, Shoot
*Rubus fruticosus* - Blackberry; found in Plant
*Salvia officinalis* L. - Sage; found in Leaf, Stem
*Salvia sclarea* L. - Clary Sage; found in Plant
*Salvia triloba* L. - Greek Sage; found in Plant TABLE 1-continued

*Sambucus nigra* L. - Black Elder, Elder, European Alder, European Elder, European Elderberry; found in Bark, Flower, Leaf
*Sanguisorba officinalis* L. - Greater Burnet; found in Plant
*Satureja hortensis* L. - Summer Savory; found in Leaf, Stem
*Satureja montana* L. - Savory, Winter Savory; found in Plant
*Sorbus aucubaria* L. - Rowan Berry; found in Fruit
*Syringa vulgaris* L. - Lilac; found in Leaf
*Teucrium chamaedrys* L. - Wall Germander; found in Plant
*Teucrium polium* L. - Golden Germander; found in Plant
*Teucrium scordium* - Water Germander; found in Plant
*Teucrium scorodonia* L. - Germander, Wood Germander; found in Leaf
*Thevetia peruviana* (PERS.) K. SCHUM. - Adelfa Amarilla (Sp.), Cabalonga (Sp.), Chirca (Sp.), Loandro-Amarelo (Port.), Luckynut, Oleandre Jaune (Fr.), Peruvian Yellow Oleander, Thevetie (Ger.), Yellow Oleander; found in Leaf
*Thymus serpyllum* L. - Creeping Thyme; found in Plant
*Thymus vulgaris* L. - Common Thyme, Garden Thyme, Thyme; found in Plant
*Uncaria tomentosa* DC - Cat's Claw, Garabato Amarillo, Una de Gato; found in Plant
*Vaccinium corymbosum* L. - Blueberry; found in Plant
*Vaccinium myrtillus* L. - Bilberry, Dwarf Bilberry, Whortleberry; found in Fruit, Leaf
*Vaccinium vitis-idaea* var. *minus* LODD. - Cowberry, Lingen, Lingonberry; found in Fruit
*Verbena officinalis* L. - Vervain; found in Plant
*Viburnum opulus* subsp. var. *opulus* - Crampbark, European Cranberry Bush, Guelder Rose, Snowballbush; found in Fruit
*Viburnum prunifolium* L. - Black Haw; found in Bark
*Vinca minor* L. - Periwinkle, Running-Myrtle; found in Leaf, Plant
*Zizyphus jujuba* MILL. - Da-Zao, Jujube, Ta-Tsao; found in Plant The best known representatives of the plant kingdom having proven COX-2 inhibitory activity are aloe, green tea extracts, red currants and sweet cherry, scilla, ginger, curcuma and ginkgo.

Since collagen and its hydrolysis product gelatin is known to have only an infinitesimal anti-inflammatory action, the object of the present invention is to provide a new physiologically active composition based on collagen which, in addition to the known good effect of collagen in particular on degenerative joint diseases, also has the property of acting positively on inflammatory processes above all in the joint region or to support such positive effects. In doing so the primary aim was for the new composition to provide a variant that can be easily administered and which does not give rise to any problems with regard to compliance. Furthermore, the active components should not result in any negative accompanying phenomena whatsoever which is why they should be derived in particular from natural sources. The aim was also to avoid any negative interaction between the physiologically active main components so that the collagen component as well as the other components having the desired physiological activities are utilized fully for the prevention and treatment especially of degenerative joint diseases.

This object is achieved with an appropriate composition containing enzymatically hydrolysed collagen as the active component I and an active component II having anti-oxidative and/or anti-inflammatory properties.

During the testing of representative compositions according to the invention it was completely surprisingly found that the known good effect of the collagen component was not weakened in any way in the claimed composition but rather that particularly the joint protecting/stabilizing effect of collagen was not only additively increased by the other physiologically active component II but was rather considerably synergistically increased. Thus it was possible not only to maintain or increase the functional status mainly due to the collagen component but rather it was possible to significantly improve the pain condition by administering the claimed composition in the case of chronic inflammatory processes. This synergistic effect of the two components I and II clearly exceeds the effect of the individual substances which was not to be anticipated to this extent.

With regard to component I it has proven to be advantageous within the scope of the present invention when this component has an average molecular weight of 1 to 10 and particularly preferably of 2 to 6 kilodaltons. A component I having an average molecular weight of 2 to 4 kilodaltons is especially preferred. A component I of animal origin in which the collagen is for example of bovine or porcine origin and is derived from their bones, skin and connective tissue is also well suited in the sense of the present invention.

Since the present composition should not be associated with any limitations whatsoever with regard to a specific form of application, it has proven to be advisable to use a collagen that is soluble in cold water as component I in the composition according to the invention.

In connection with component II the present invention envisages that it is of biological origin where variants based on a fermentation broth and/or an extract are regarded as preferred. The fermentation broth can also be used in an untreated form when the compounds contained therein having anti-oxidative and/or anti-inflammatory properties are present in effective amounts. The extracts that are also preferred can be liquid variants which are present either as aqueous extracts or alcoholic products or are derived from them in powder form by drying processes. With regard to the extracts as a preferred variant for component II, extracts of plant origin are encompassed by the present invention as being particularly preferred.

Since an extremely wide range of possible variants come into consideration as component II for the use according to the invention, the only criterion is, as already mentioned, its effect in combination with component I. However, for reasons of administration and compliance it is regarded as preferred within the scope of the invention when component II is an extract, a lyophilisate and/or a fraction where these three administration variants should be derived in particular from plantago species such as *Plantago mayor, Plantago media* or *Plantago lanceolata*, from *Aloe vera, Aloysia triphylla, Humulus lupulus, Ginko biloba, Lippia triphylla* and/or *Lippia citriodora*.

The latter plant species are particularly suitable in the present connection because their active ingredients include flavonoids and they exhibit anti-oxidative properties in the form of trolox equivalents and can thus be used as matrix protectors for inflammatory disease forms which have been triggered by or amplified by reactive oxygen species.

In particular extracts of *Aloysia triphylla* well-known as Lemon Verbena are used traditionally in France for the symptomatic treatment of indigestion on the one hand, and also nervousness and sleep disorders, on the other hand.

Among the large number of compounds and classes of compounds having anti-oxidative and/or anti-inflammatory properties that come into consideration for component II, those have proven to be particularly suitable for the claimed composition which contain phenylethanoids and particularly preferably acteosides and/or a COX-2 inhibitor such as e.g. the known α and β acids from hops, apigenin, baicalein, berberin, cinnamaldehyde, cirsilineol, curcumin, eugenol, kaempferol, oleandic acid, quercetin, resveratrol, salicylic acid and ursolinic acid.

Ribwort species (plantago spec.) contain iridoid glycosides, flavones, phenol-carboxylic acids, coumarins, phenylethanoids and polysaccharides as active ingredients. The following glycosides were determined from the flavone class of compounds: apigenin-7-O-glucoside, apigenin-6,8-di-C-glucoside, apigenin-7-O-glucuronide, apigenin-7-O-glucoronylglucoside, luteolin-7-O-glucoside, luteolin-7-O-glucuronide, luteolin-7-O-glucuronide-3'-O-glucoside and luteolin-7-O-glucuronyl glucoside. Prominent representatives of the phenolcarboxylic acids in plantago are chlorogenic acid and cistanoside as well as 4-hydroxybenzoic acid, protocatechuic acid, gentisinic acid etc.; aescolitin is also present as a typical coumarin. The phenylethanoids that are also present in plantago are a group of ingredients whose essential structural feature comprises the formation of a full acetal from glucose and phenylethanol as well as an ester of caffeic acid with glucose. For example about 3.5% acteoside (verbascoside) and about 1% plantamajoside were isolated from *Plantago lanceolata*. Other phenylethanoids are isoacteoside and lavandulifolioside.

The already mentioned acteosides are naturally occurring disaccharides with acute and chronic anti-inflammatory activity. Acteoside inhibits the formation of eicosatetraenoic acid derivatives (5-HET) and leucotriene $B_4$ in human peripheral polymorphonuclear leucocytes, both of which play an important role in inflammatory processes. However, acteosides as well most of the phenylethanoids also have interesting anti-oxidative properties since they can dose-dependently inhibit the $Fe^{2+}$/ADP-induced lipid oxidation of mitochondrial and liposomal lipids from rat liver. In this process they develop among others radical scavenger activities on superoxide anion and hydroxyl radicals. In addition it was demonstrated that acteosides are able to protect chondroitin sulfate as an important component of the cartilaginous mass from decomposition by oxygen radicals.

The present invention is in no way limited to the said plant species although these are preferred due to their easy accessibility and processability. However, suitable preparations of plants also come into consideration as component II such as those listed for example in table 1 of this description.

The breadth of the claimed composition also arises from the weight ratio in which components I and II can be present in the claimed composition. This is not at all limited to a certain mixing ratio but rather covers a relative broad range for the components which in particular should be present in a weight ratio I:II of 1:0.01 to 0.5, preferably 1:0.001 to 1 and particularly preferably 1:0.0001 to 10.

As is clearly documented by the wording of the claim, the present composition is not limited to the two components I and II but rather must "merely" contain these two components. For this reason the present invention also envisages a composition which apart from these two main components I and II, additionally contains further physiologically active components such as glucosamine, chondroitin, hyaluronic acid, methylsulfonylmethane and creatine or suitable derivatives thereof.

The main selection criterion for these additional physiologically active components is their positive effect on usually inflammatory symptoms such as those that occur especially in degenerative joint diseases, or their contribution to a successful prevention which is why components which quite generally support anti-oxidative and/or anti-inflammatory mechanisms of action or exert a positive effect on the maintenance or the synthesis of cartilaginous mass or periosteum are of top priority.

However, the present invention also envisages that the composition contains general formulation auxiliaries and/or stabilizing agents, fillers, flavourings, dyes and sweeteners which serve to preserve the selected form of administration or increase the compliance.

The claimed composition is not primarily intended for use in the traditional pharmaceutical/medical fields but rather its administration as part of self indication such as the so-called free sale OTC products. For this reason the present invention envisages that the claimed composition is offered and administered in the form of food supplements, functional foods and cosmetic preparations where in particular tablets, capsules, dragees, bars, granules, powders, stable solutions and juices are particularly suitable forms of administration.

As already mentioned several times the claimed composition should be beneficial especially for degenerative joint diseases. For this reason the invention, in addition to the actual composition, also claims its use where most importance is attached to the production of an agent for the prevention and/or treatment of inflammatory and/or degenerative symptoms especially those with a chronic course and particularly preferably arthritis, arthroses and pathogenic angiogenesis. The agent obtained in this manner is suitable within the scope of the present invention especially for use by professional, leisure and recreational athletes which are exposed to an increased strain on the joints especially in the knee region, and also by older and reconvalescent persons and in this case again especially persons with joint functions that are under particular strain and/or impaired.

Due to the possibility of combining their actions which, on the one hand, originate from the collagen and, on the other hand, from the anti-inflammatory/anti-oxidative properties of component II, the claimed composition and the agents produced therewith are particularly suitable for the prevention of joint overstrain and the associated functional limitations and degeneration processes and they are also suitable for their treatment.

In this connection the actual action cannot be regarded as being limited to an increase in the cartilaginous mass on balance but rather that the degradation or decrease in cartilaginous mass is prevented or counteracted. In this process the formation of cartilaginous mass may indeed be promoted or cartilaginous mass may be newly formed which does not necessarily have to be associated with an overall increase in cartilaginous mass. Hence within the scope of the present invention the claimed composition is thus primarily used to maintain the total cartilaginous mass in a balanced manner.

The special use which is also claimed by the present invention is additionally characterized in that the agent that is obtained is administered in such amounts that it corresponds to a daily dose of component I of <10 g, preferably <5 g. It is also provided that the agent that is obtained is administered continuously over a period of 2 weeks to 6 months and preferably of 3 weeks to 3 months which should be preferably orally.

The benefit achieved with the present invention can thus also be regarded as the fact that the amount of collagen or gelatin to be administered can now be reduced from amounts of considerably more than 10 g/day to significantly smaller amounts than 10 g and moreover the previously usual period of application of >8 weeks can also be considerably shortened. Since the considerably reduced daily dose/total dose of component I does not in any way reduce its effectiveness in the composition according to the invention, it may be assumed that there is a marked synergistic increase in efficacy that is due to the combination according to the invention of component I with component II, but however, the exact mechanism of action cannot yet be stated in each case.

The following study which is shown as an example demonstrates this positive effect of the claimed composition.

EXAMPLES

The effectiveness of a combination preparation designed as a food supplement was examined in patients with knee-joint arthrosis in a double blind and placebo-controlled study. The composition that was used comprised the product "Arthred" (collagen hydrolysate from the Degussa Food Ingredients GmbH) and the special extract "Planox L" (from Anoxymer GmbH) as the sole components. "Arthred" consists of an enzymatically hydrolysed bovine collagen and contains exclusively short-chain peptides having a molecular weight of about 3 kilodaltons where the chain length is about 25 to 30 amino acids. "Planox L" was isolated from the dried herb of *Aloysia triphylla* (L'Her.) O. Kuntze/Prit. (syn. *Lippia citriodora* H.B.K., *Lippia triphylla* (L'Her.) O. Kuntze) by an aqueous-alcoholic extraction. The extract contains flavonoids and at least 10% by weight of the phenylethanoid acteoside as the active ingredient.

The test persons comprised ambulatory, male and female patients with knee joint arthroses.

The aim of the study was to optimize the general state (improvement of the symptoms) of mild knee joint arthroses while assessing the pain condition and functional status by means of the Lequesne index and WOMAC index (Western Ontario and McMaster Universities). The study was designed as a double blind, placebo-controlled and randomized short term study in patients with knee joint arthroses and the study was carried out as a 4-armed study placebo vs. Planox L vs. Arthred vs. Planox L+Arthred each with 25 test persons and a total study size of 100 test persons with oral administration in each case. The treatment period was set at 6 months per patient.

The inclusion criteria were mild cases of knee joint arthroses; state after arthroscopy without deep-reaching defects in the cartilage; unlimited age groups; male and female sex.

The following were defined as exclusion criteria: rheumatic diseases; infections (especially joint infections); severe cases of knee joint arthroses; ligament, cartilage replacement and joint operations (apart from arthroscopy); NSAR/corticoid/antibiotic medication (apart from lipid-lowering drugs, antihypertensives, anti-arrhythmic drugs); administration of vitamins, minerals and phytotherapeutic agents and in particular plant extracts from the rampian and artichoke as well as Wobenzyme-hyaluronic acid injections.

The study medication was carried out as follows:

| | |
|---|---|
| Planox L: | 1 g Plantox L 1 × daily (10% acteoside (=100 mg acteoside daily) + 5 g cellulose) |
| Arthred: | 5 g collagen hydrolysate 1 × daily |
| Planox L + Arthred: | 1 g Planox L + 5 g collagen hydrolysate 1 × daily |
| Placebo: | 5 g microcrystalline cellulose 1 × daily |

At the beginning of the study the BSG value and the radiological data (X-ray pictures) were collected for each patient. Optionally synovial fluid was collected from the knee joint by puncture. The pain condition and functional status of the knee joint was also determined with the aid of the appropriate indices. In addition the pain condition and the functional status of the knee joint was monitored every 6 weeks i.e. in week 6, 12, 18 and 24 after the start of the study.

Results:

Arthred and Planox L exhibited no improvement or a non-significant improvement when administered alone (comparative experiments). A synergistic effect surprisingly occurred with the composition according to the invention consisting of a combination of Arthred+Planox L which considerably exceeded the effect of the individual substances. When the combined composition was administered, the pain condition was significantly reduced and the functional status of the knee joint was considerably increased.

The invention claimed is:

1. A composition comprising enzymatically hydrolyzed collagen, an anti-oxidative and anti-inflammatory substance which is not a vitamin wherein said substance is a fermentation broth or an extract of plant origin, wherein said extract of plant origin is from *Aloysia triphylla* and wherein said composition is an oral composition.

2. The composition of claim 1, wherein the average molecular weight of said enzymatically hydrolyzed collagen is from about 1 to about 10 kilodaltons.

3. The composition of claim 1, wherein the average molecular weight of said enzymatically hydrolyzed collagen is from about 2 to about 6 kilodaltons.

4. The composition of claim 1, wherein the average molecular weight of said enzymatically hydrolyzed collagen is from about 2 to about 4 kilodaltons.

5. The composition of claim 1, wherein said enzymatically hydrolyzed collagen is of animal origin.

6. The composition of claim 1, wherein said enzymatically hydrolyzed collagen is soluble in cold water.

7. The composition of claim 1, further comprises a phenylethanoid, which is acteoside or isoacteoside.

8. The composition of claim 1, wherein a weight ratio of said enzymatically hydrolyzed collagen to said substance is 1:0.0001 to 10.

9. The composition of claim 1, further comprising a second substance selected from the group consisting of glucosamine, chondroitin, hyaluronic acid, methylsulfonylmethane, creatine, a formulation agent, a stabilizer, a filler, a flavoring, a dye and a sweetener.

10. The composition of claim 1, wherein said composition is in the form of a tablet, a capsule, a dragee, a bar, a granule, a powder, a solution or a juice.

11. A method for treating an inflammatory or degenerative symptom of one of arthritis, arthroses and pathogenic angiogenesis, comprising administering a therapeutically effective amount of the composition of claim 1 to a subject in need thereof.

12. The method of claim 11, wherein said composition is administered continuously over a period of about 2 weeks to about 6 months.

13. The method of claim 11, wherein said composition is administered continuously over a period of about 3 weeks to about 3 months.

14. A method for treating strained or impaired joint function comprising administering a therapeutically effective amount of the composition of claim 1 to a subject in need thereof.

15. The method of claim 14, wherein said composition is administered continuously over a period of about 2 weeks to about 6 months.

16. The method of claim 14, wherein said composition is administered continuously over a period of about 3 weeks to about 3 months.

* * * * *